United States Patent [19]

Savage et al.

[11] Patent Number: 5,507,725
[45] Date of Patent: *Apr. 16, 1996

[54] STEERABLE CATHETER

[75] Inventors: Steven D. Savage, Brooklyn Center; Gregory G. Brucker, Minneapolis, both of Minn.

[73] Assignee: Angeion Corporation, Plymouth, Minn.

[*] Notice: The portion of the term of this patent shall not extend beyond the expiration date of Pat. No. 5,368,564.

[21] Appl. No.: 173,250

[22] Filed: Dec. 22, 1993

Related U.S. Application Data

[63] Continuation-in-part of Ser. No. 996,090, Dec. 23, 1992, Pat. No. 5,368,564.

[51] Int. Cl.$^6$ .................................................. A61M 37/00
[52] U.S. Cl. ........................................................... 604/95
[58] Field of Search ............................ 604/95, 280–282; 128/4, 786, 772

[56] References Cited

U.S. PATENT DOCUMENTS

| | | |
|---|---|---|
| 3,437,091 | 4/1969 | Jerushalmi et al. . |
| 3,470,876 | 10/1969 | Barchilon . |
| 3,618,614 | 11/1971 | Flynn . |
| 3,680,544 | 8/1972 | Shinnick et al. . |
| 4,236,525 | 12/1980 | Sluetz et al. . |
| 4,576,772 | 3/1986 | Carpenter . |
| 4,627,844 | 12/1986 | Schmitt . |
| 4,636,346 | 1/1987 | Gold et al. . |
| 4,765,220 | 8/1988 | Bach . |
| 4,790,831 | 12/1988 | Skribiski . |
| 4,801,297 | 1/1989 | Mueller . |
| 4,850,351 | 7/1989 | Herman et al. . |
| 4,898,577 | 2/1990 | Badger et al. . |
| 5,056,517 | 10/1991 | Fenier . |
| 5,083,565 | 1/1992 | Parins . |
| 5,125,909 | 6/1992 | Heimberger . |
| 5,152,748 | 10/1992 | Chastagner . |
| 5,199,950 | 4/1993 | Schmitt et al. . |
| 5,273,535 | 12/1993 | Edwards et al. . |

OTHER PUBLICATIONS

Bard Electrophysiology Price List (Effective Jan. 1, 1991).
The SteeroCath™ Catheter product literature form EP Technologies, Mountain View, CA (date unknown).
"Management's Discussion and Analysis of Financial Condition and Results of Operations", EP Technologies, Mountain View, CA, front p. 17 of EP Technologies, Inc. Prospectus, Mar. 1993.
Voyagr™ Series Fully Steerable Catheters product literature from CardioRhythm, San Jose, CA (date unknown).
Torqr™ Series Electrode Catheters product literature from CardioRhythm, San Jose, CA (date unknown).
RF Ablatr™ Fully Steerable Therapeutic Catheters product literature from CardioRhythm, San Jose, CA (date unknown).
Innovations in Electrophysiology product literature and price list from Webster Laboratories, Inc., Baldwin Park, CA (price list dated Apr. 1992).
"Increase in the Lesion Size and Decrease in the Impedance Rise With a Saline Infusion Electrode Catheter for Radiofrequency Catheter Ablation", abstract by Stephen Huang.
"Porous Metal Tipped Catheter Produces Larger Radiofrequency Lesions Through Tip Cooling", abstract by Dennis Bergau.

(List continued on next page.)

*Primary Examiner*—C. Fred Rosenbaum
*Assistant Examiner*—Frank Wilkens, III
*Attorney, Agent, or Firm*—Patterson & Keough

[57] ABSTRACT

The invention relates to a steering system for a catheter tip. The system includes wire members that extend through a catheter wall that are used to pull a distal portion of the catheter tip causing controlled, predetermined bending at the tip. Anchoring members located near the catheter tip connect the distal end of the catheter with wire members. The steering system also contains control members which are located at a proximal portion of the catheter and are used to control the pull on the wire members. Steering enhancement members are also included in the steering system which facilitate the bending of the catheter wall.

5 Claims, 7 Drawing Sheets

OTHER PUBLICATIONS

"Comparison of Titanium–Mesh and Porous Disk Electrodes For Epicardial Defibrillation", Rubin, L., Rosenberg, D., Parsonnet, V., Villaneuva, A., Ferraryan, M., *Pace–Pacing and Clinical Electrophysiology*, 1991, V4, N11, P 1860–1864.

"Early Evolution of Electrical Parameters of a New Implanted Porous Catheter", Pauletti, M., Contini, C., Garberoglio, B., Chinaglia, B., *Pace–Pacing and Clinical Electrophysiology*, 1981, V4, N3, PA 92.

"Temperature Distributions Induced in Pig–Tissues by a Water–Cooled Disk Electrode RF–System", Prionas, S. D., Hahn, G. M., *Medical Physics*, 1984, V11, N1, P 22–25.

"Evaluations of a New Unipolar Endocardial Catheter With Porous Tip (Wire Mesh) Electrode—Early Results of Pacing Thresholds, Intracardiac Voltage and Stability Characteristics", Vera, Z., Klein, R., Mason, D. T., McMillin, D., Dajee, A., *Clinical Research*, 1980, V28, N2, PA 218.

Abstract of Japanese Patent, JP 04231062 A (no copy of patent available).

Abstract of U.S. Pat. No. 4,976,711 (no copy of patent available).

Abstract of U.S. Pat. No. 5,125,928 A (no copy of patent available).

Fig. 2C

STEERABLE CATHETER

REFERENCE TO PRIOR APPLICATIONS

This is a Continuation In Part application of Ser. No. 07/996,090 now U.S. Pat. No. 5,368,564 filed Dec. 23, 1992.

1. Field of the Invention

This invention relates to a steerable catheter which is utilized in laser surgery. In particular, the invention relates to a steering system for a catheter tip which achieves greater control of the catheter tip movement.

2. Background of the Invention

Catheters have been utilized in the medical industry for many years. One of the greatest challenges in using a catheter is controlling the position and placement of the catheter tip from a remote location outside of the patient's body. Some catheters have features designed to aid in steering the catheter and overcoming this challenge.

However, several significant problems are still encountered with these catheters. The devices typically have preformed inner catheters which are placed in an outer guiding sheath. When the inner catheter is extended or the sheath withdrawn, the inner catheter assumes a different shape. It is usually necessary to draw the inner catheter back into the outer guiding sheath to reshape the catheter tip, and then extend the inner catheter out of the outer sheath for each successive use in another location.

Steerable catheters generally have closed, solid or substantially solid central areas rather than hollow central lumens because of the tendency of lumened steerable catheters to collapse and greater ease of bending around the center axis of a catheter. Since the lumen region is solid, it is not possible to pass another structure, such as a laser catheter, through the steerable catheter.

Steerable catheters exhibit different properties when positioned in a patient's body rather than outside the body. After insertion into the body, the material of the steerable catheter is warmed, and the catheter may absorb water. As a result, the steerable catheter may not perform as desired because of the change in the plastic characteristics.

Also, known steerable catheter distal tips exhibit non-fluid movements. The catheter distal tip often bends with only exaggerated and imprecise movements. A locking cam must be tightened or the handle held in place once the tip is in place during the medical procedure, which also contributes to imprecise movements of the tip. These devices also lack the ability to make very small movements, such as tight radius turns. Also, wire controlled steerable catheters may experience undesired wire deformation over time which affects control.

Torque has also been a significant disadvantage encountered with known steerable catheters. As the steerable catheter travels through the body, different drag forces are created on the catheter. A loss in torque results, and additional power to make the catheter proceed through the body is required.

Another type of steerable catheter uses a bellows which aids in catheter bending. The bellows stretches and collapses as the catheter is moved. However, in steerable catheters having a bellows configuration, the inner surface of a central lumen of the catheter is often configured so that passage of any structure through the central lumen, such as a laser catheter, is impaired.

SUMMARY OF THE INVENTION

The present invention relates to a steerable catheter which includes an elongate catheter body having a circular wall. Wire members extend through the catheter wall to pull on a portion of the catheter wall and the catheter tip. The steerable catheter also includes anchor members located along the length of the catheter body for connection with the distal end of the wire members. A control member located at the proximal end of the catheter is used to control the pull on the wire members. A steering enhancement structure also makes up a part of the steerable catheter, including a portion of the catheter wall having shaped radial indentations which facilitate the bending of the catheter wall. A lumen extends the length of the catheter.

The invention also relates to a steering enhancement structure which improves the maneuverability of a medical catheter. The steering enhancement structure comprises a catheter body which has a catheter wall. A radial indentation region is positioned within the catheter wall.

The invention also relates to a steerable catheter which permits the passage of a biologically compatible fluid comprising a catheter body having a circular wall. A catheter tip and a ring electrode are positioned at the distal end of the catheter body. Wire members extend through the catheter wall to pull on a portion of the catheter wall and the catheter tip. The steerable catheter also includes anchor members located along the length of the catheter body for connection with the distal end of the wire member. A control means is located at the proximal end of the catheter to control the pull on the wire members. A steering enhancement structure also makes up part of the steerable catheter, including a portion of the catheter wall having shaped radial indentations which facilitate the bending of the catheter wall. A lumen extends the length of the catheter. Passage means are located within the catheter tip and the ring electrode for the passage of a biologically compatible fluid.

DETAILED DESCRIPTION OF THE INVENTION

The invention is a steerable catheter which is highly maneuverable. The medical catheter comprises radial indentations in the catheter wall, a large central lumen, and is partially controlled by the pulling and releasing of wire members attached to anchoring rings positioned along the length of the catheter.

Figure 1:
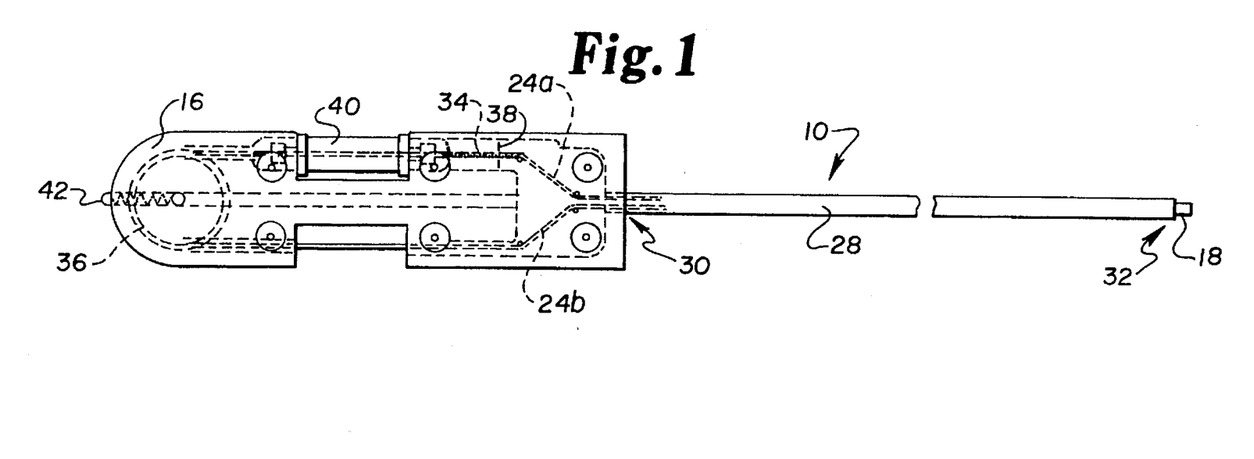
FIG. 1 is a side view of the catheter of the present invention.
Figure 2A:
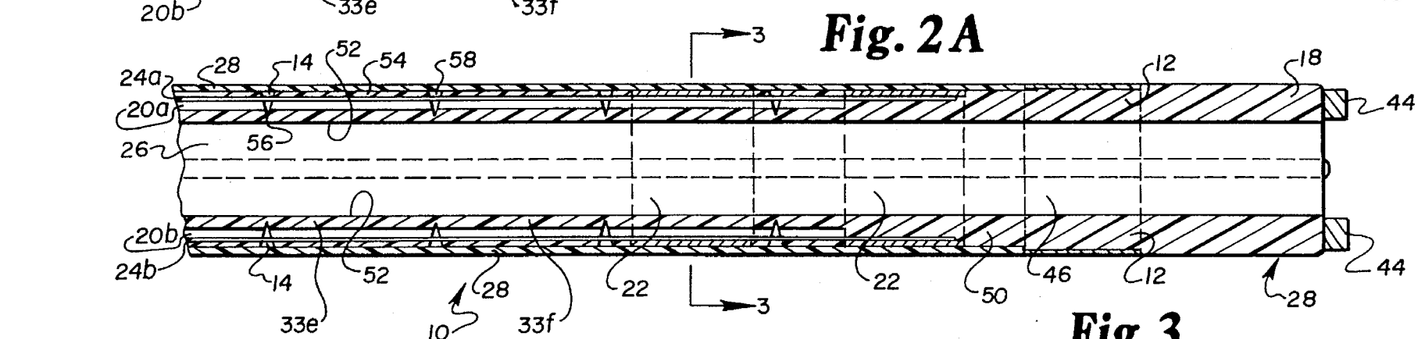
FIG. 2A is side sectional view of a portion of the catheter.

Referring to FIGS. 1 and 2A, steerable catheter 10 includes catheter body 12, steering enhancement means or notches 14, platform handle 16, distal tip 18, wire access lumens 20a, 20b, steering or anchoring rings 22, pull wires 24a, 24b, central lumen 26, and outer sheath 28.

Guiding or outer sheath 28 is positioned over and extends along a length of the catheter body 12 between platform handle 16 and distal catheter tip 18, and is generally circular in cross section. Outer sheath 28 may be attached to catheter body 12. The length of catheter body 12 and the length of outer sheath 28 may vary depending on the distance to the site at which the catheter will be utilized. Outer sheath 28 is preferably made from a biologically compatible thermoplastic material which has some resilience, compression, and elasticity properties. Preferred materials include urethane and nylon elastomers. Outer sheath 28 may be optionally coated with an anti-thrombolytic material. Outer sheath 28 provides structural strength to catheter 10 and also prevents passage of blood or tissue into catheter 10.

Catheter shaft or catheter body 12 is tubular and is generally circular in cross section. Catheter body 12 is preferably made from a biologically compatible thermoplastic material which has some resilience, compression, and elasticity properties. Preferred materials include urethane and nylons.

Figure 2B:
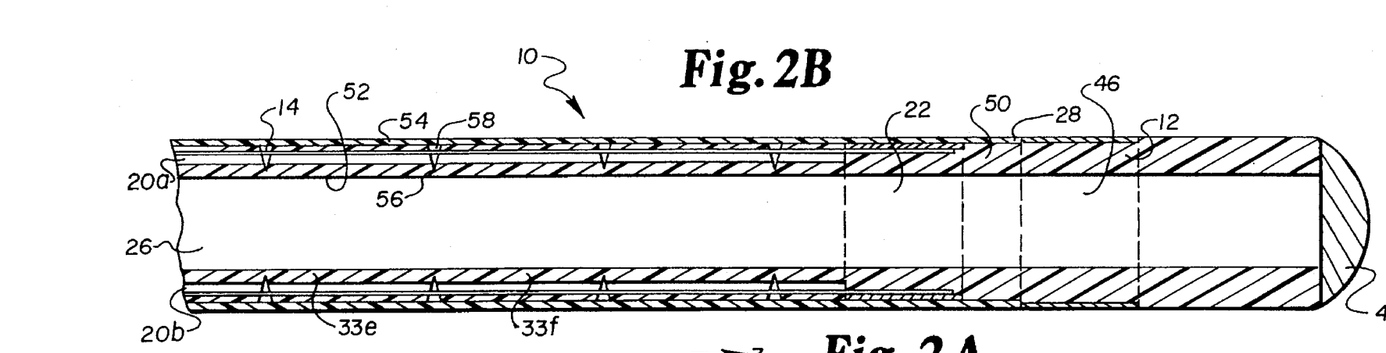
FIG. 2B is a side sectional view of a portion of an alternate embodiment of the catheter shown in FIG. 2A.

Consecutively softer, lover durometer materials may optionally be utilized along the length of the catheter body 12 as catheter 10 progresses from the proximal end 30 adjacent handle 16 towards distal end 32. In addition, distal end 32 of catheter body 12 of catheter 10 may comprise lower durometer materials, and the proximal end 30 of catheter body 12 may comprise higher durometer materials. Also, catheter body 12 may comprise a distal portion having a plurality of durometers progressing preferably axially from the proximal end of the distal portion of catheter body 12 to the distal end of catheter body 12 to provide increased pliability proximate the distal end of catheter body 12. Alternatively, catheter body 12 may comprise longitudinally extending wedge regions comprising different durometer materials, as shown by regions 33a, 33b, 33c, 33d in FIG. 2D. In addition, the higher and lower durometer materials used in catheter body 12 at distal end 32 may overlap. As shown in FIG. 2E, a higher durometer material 31 is proximate central lumen 26 of catheter 10, with a lower durometer material 37 proximate outer sheath 28 of catheter 10. Material 37 may be of only one durometer, having a lower durometer than material 31. For example, as shown in FIG. 2E, catheter body 12 may have tapered, longitudinally extending wedge regions comprising different durometer materials, as shown by regions 35a, 35b, 35c, 35d. Preferably, 35a is of a higher durometer than 35b, and 35a is of a higher durometer material than 35d. Regions 35a, 35b, 35c, 35d are of a lower durometer than material 31. Regions 35a, 35b, 35c, 35d are preferably circumferential, and may be radial, with respect to catheter body 12. As shown in FIG. 2E, the wedge or tapered shape of regions 35a–d overlap axially and comprise a material composition having mechanical characteristics differing from the characteristics of the adjacent regions. Catheter 10 may include numerous regions 35 of varying durometers throughout the length of the catheter. Preferably, regions 35 of varying durometers do not extend beyond anchoring rings 22. Preferably, the area between anchoring rings 22 and tip 18 is of one durometer. Preferably, catheter body 12 material becomes progressively softer and more pliable at distal end 32 with the use of progressively softer, lower durometer plastic materials, for example, portion 33e compared with portion 33f, as shown in FIG. 2B. Stiffer, higher durometer plastics are preferably utilized for the main part of catheter body 12.

Platform handle 16, shown schematically in FIG. 1, controls the movement of steerable catheter 10 through the body. Handle 16 may contain a threaded rod 34 and a pulley mechanism 36, shown in FIG. 1, to control the pull on one or more pull wire members 24 and the movement of catheter tip 18. Wires 24a, 24b are positioned adjacent threaded rod 30. Bearing 38 is positioned on one end of threaded rod 34, and knurled knob 40 is positioned along the length of threaded rod 34. A spring or screw 42 is adjacent pulley mechanism 36. Threaded rod 34 locks the position of steerable catheter 10. Exerting pressure on spring or screw 42 actuates wires 24a, 24b giving positive movement of wires 24, so there is less tension on catheter 10. Actuation of wires 24 causes wires 24 to move forward or backwards so that catheter 10 moves in the desired direction. As knob 40 is engaged, rod 34 does not rotate because bearing 38 creates positive locking of catheter tip 18 without use of force. Positive locking is advantageous since it prevents movement of the catheter tip 18 once catheter 10 is positioned at the desired site within the patient. Spring 42 and pulley mechanism 36 keep tension in the system to alleviate any slack in the system. In one embodiment, a thumb screw (not shown) is utilized to move catheter tip 18 forward or backward in the patient's body. Use of this type of system permits catheter 10 to move smoothly and in fluid motion within the patient's body.

Alternatively, platform handle 16 may comprise a servomechanism which pushes and pulls on wires 24 to control the pull on wire members 24 in catheter 10 and the movement of catheter tip 18. Alternatively, handle 16 may comprise a worm gear coupled to another gear. As knob 40 is spun, the worm gear turns, thereby turning pulley mechanism 36 on which wires 24a, 24b are positioned. These systems also provide positive locking of catheter tip 18 in any position, without using any force. Catheter tip 18 remains locked in position until spring or screw 42, the worm gear, or the servomechanism is actuated, turned or engaged.

Referring to FIG. 2A, distal tip 18 is positioned at the distal end 28 of catheter body 12 of steerable catheter 10. A device to administer laser energy may be passed through central lumen 26 of catheter body 12 to tip 18. One or more unipolar or bipolar sensing or tip electrodes 44 may also be positioned within and extend from distal tip 18. Preferably, two to four bipolar tip electrodes 44 extend from distal tip 18 in a perpendicular orientation to the tissue surface. Tip electrodes 44 may be configured to record unipolar or bipolar signals from the tissue, and may be in a bi-planar orientation. A plurality of ring electrodes 46 may also be positioned proximate tip 18 in a parallel orientation to the tissue surface. Tip electrodes 44 and ring electrodes 46 preferably comprise a metallic material. The invention, however, may be employed in various types of catheters using various catheter tips.

An alternative embodiment of catheter 10 is shown in FIG. 2B. Catheter tip 18 is solid and contains an ablation electrode 48 to administer electric energy to an affected site during the medical procedure. Generally, ablation electrode 48 is made of a metallic material.

Figure 2C:
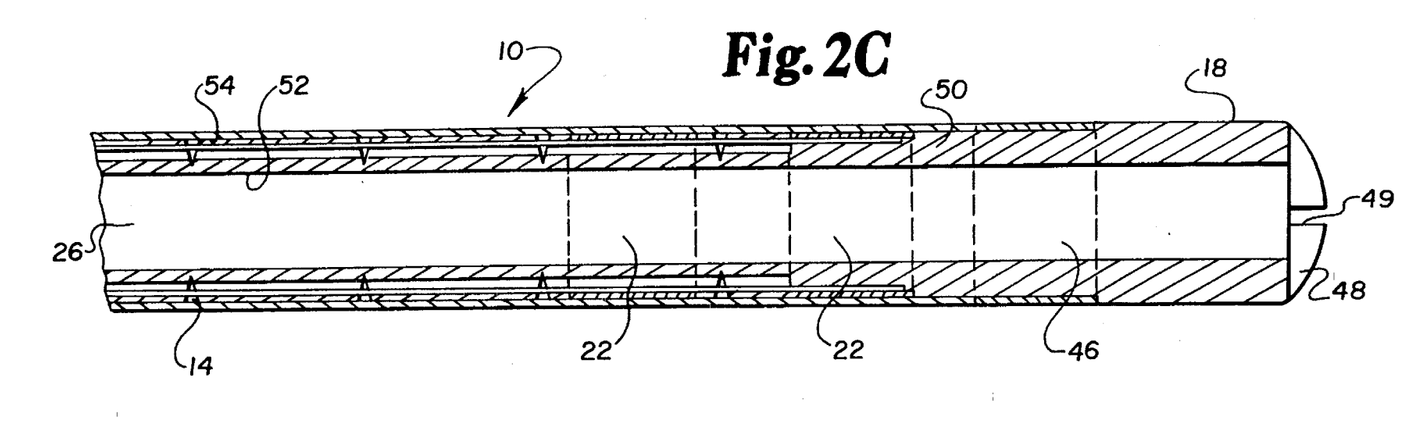
FIG. 2C is a side sectional view of a portion of an alternate embodiment of the catheter shown in FIG. 2A.

In the alternative embodiment of catheter 10 shown in FIG. 2C, catheter tip 18 and one or more ring electrodes 46 are solid with one or more smaller holes or passageways 49 to allow passage of a sterile flushing medium through and around the metallic surface. Tip 18 and ring electrodes 46 are made of a metallic material. Alternatively, tip 18 and ring electrodes 46 may be made of porous metals which may contain a plurality of small passageways 49 connecting the inner and outer surface of the metal, and permitting passage of a sterile flushing medium. In both of these embodiments, the fluid acts as a medium to bathe the catheter elements crucial to mapping and ablation, allowing them to remain free of coagulated biological materials which can alter their inherent effectiveness. This enhances mapping efficiency. In addition, the fluid is particularly important in medical procedures such as cardiac ablation in which the temperature of the metal parts of the catheter can be elevated, since the fluid reduces the temperature of the metal parts.

Referring again to FIG. 2A, wire access lumens 20a, 20b–20n extend along the length of steerable catheter 10, from platform handle 16 to tip 18, and are preferably formed with extrusion techniques. Wire access lumens 20 are generally circular in cross section and are positioned within catheter wall 50 of catheter body 12 of steerable catheter 10. Alternatively, wire access lumens may be positioned along the exterior surface of catheter 10, with sheath 28 protecting wires 24 within wire access lumens 20. In general, two to four wire access lumens are positioned preferably coaxially within catheter wall 50, although additional lumens are possible. However, due to the tendency of a multiple lumen catheter to collapse, the catheter may include a braided material to enhance structural integrity. A non-flow material, such as a plastic or metallic material, may be inserted into the multiple lumens when an outer jacket or outer sheath is positioned over the braid and the multiple lumen catheter tube. The lumens will not collapse and a circular identity will be retained when this is done. The inserted metal or plastic material is withdrawn after the outer sheath is formed. A standard thermoplastic elastomer may be used for the inner lumen. A layer of a lubricous material, such as a TEFLON brand material, may be applied to the device as a post-manufacturing step.

Figure 3:
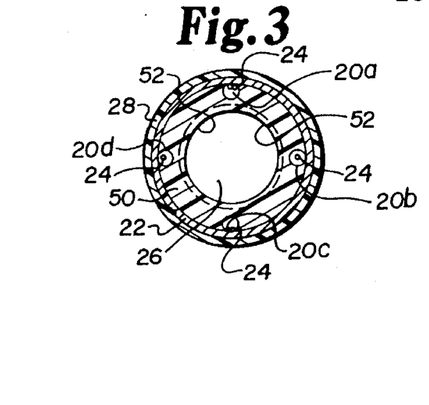
FIG. 3 is a sectional view taken along line 3—3 of FIG. 2A.

Pull wires 24a, 24b–24n are movably positioned within wire access lumens 20. Multiple wires 24 may be utilized within each wire access lumen 20 and there may be numerous lumens 20, as shown in FIG. 3. The length of wires 24a, 24b depend on the steering or anchoring ring 22 to which they are each attached. Wires 24 may have some elastic properties and may be made from a high tensile strength material such as 304 V wire, a stainless steel wire manufactured by a medical wire manufacturer, such as Fort Wayne Metals. Preferably, a wire having two times the standard wire tensile strength is utilized. However, any elasticity must be resilient and predictable to ensure restoration to original lengths and to ensure precise bending of the catheter during successive uses of the wires. Wires 24 extend through the tubular body of the catheter wall for pulling on a steerable portion of the catheter wall proximate the distal end of the catheter body to effect steering of the catheter. The steerable portion of catheter wall 50 proximate the distal end of catheter body 12 is preferably integral with catheter body 12. A plurality of wires 24 may pull on a steerable portion of the catheter wall 50 integral with and proximate to the distal end 32 of the catheter body 12.

Steering or anchoring rings 22 are generally circular in cross section and are positioned axially within a steerable portion of catheter wall 50 of steerable catheter 10. Alternatively, steering rings may be positioned around the exterior of catheter 10. Steering rings 22 extend around the circumference of catheter 10. A plurality of steering rings 22 may be positioned at various locations along the length of catheter 10, with at least two of the anchoring rings being located at axially different positions along the steerable portion of the catheter. Preferably, steering rings 22 made from a metallic material such as stainless steel are utilized in steerable catheter 10. Wires 24 are attached at the distal end to steering ring 22 or tip 18, and at the proximal end to platform handle 16. The distal end of wires 24 are preferably attached to the same steering ring 22. However, the distal end of wires 24 may be attached to distinct steering rings 22. Wires 24 attached to a steering ring 22 permits catheter 10 to bend and to be maneuvered along the length of catheter 10 as wires 24 are pulled. This construction is not limited to only maneuvering distal tip 18, but also to providing steerability to other parts of catheter 10. Wires 24 are preferably silver soldered to steering ring 22 although other connection means may be utilized.

Referring to FIG. 3, an end section view of catheter 10 is shown. Catheter wall 50 is preferably thin and is generally tubular, comprising a substantially small percentage of the diameter of catheter 10. Preferably, catheter wall 50 is approximately 0.01 inches in thickness although sizes will vary based upon the desired use. Notches 14 are positioned within catheter wall 50. Wire access lumens 20a, 20b, 20c, 20d containing wires 24a, 24b–24n are positioned within catheter wall 38 of catheter 10. The interior surface 52 of catheter wall 50 defines a substantially straight central lumen 26, and surface 52 is preferably smooth and continuous, without segmentation. Central lumen 26 is substantially open, extends along an axial length of catheter 10, and comprises a relatively large percentage of the diameter of catheter 10, and a substantial portion of the axial cross-section of the catheter. Preferably, at least fifty percent (50%) of the outer diameter of catheter 10 comprises central lumen 26, and most preferably, eighty percent (80%) of the outer diameter of catheter 10 comprises central lumen 26. For instance, in a six french catheter 10, central lumen 26 may be approximately four french in size. However, these ratios may vary. Central lumen 26 may be used to insert other types of catheters through catheter 10 without removal of catheter 10, as shown in FIG. 2A. Therefore, catheter 10 acts as a guiding catheter through which other catheters may be inserted. It is preferable that surface 52 be smooth so that other catheters may be easily passed through lumen 26.

Figure 4:
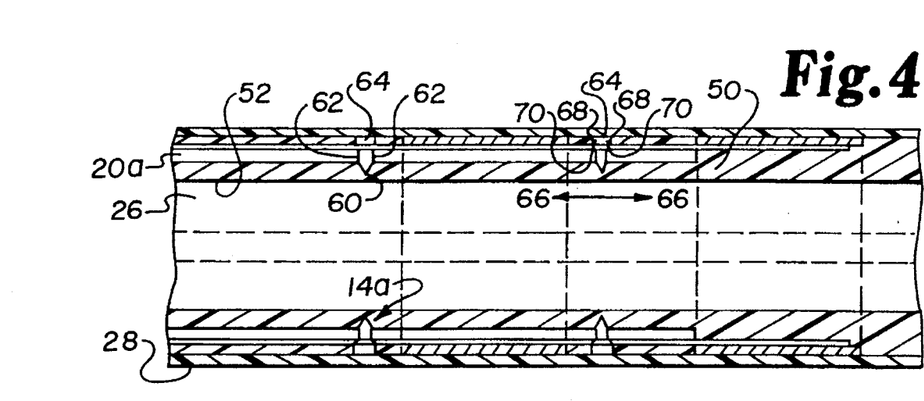
FIG. 4 is a side sectional view of an alternate embodiment of a steering enhancement means of the catheter.

FIGS. 2A, 2B, 2C, and 5 show how steering enhancement means or notches 14 are positioned along a length or steerable portion of catheter wall 50 between outer surface 54 and interior surface 52 of catheter wall 50, without intersecting the outer surface 54 or the interior surface 52 of the catheter wall 50. Preferably, notches 14 are radial indentations in catheter wall 50 which do intersect wire access lumens 20. As shown in FIGS. 2 and 4, notches 14 may be varied in shape, such as V-shaped indentations, or multiple fulcrumed configurations. Notches 14 may be molded into catheter wall 38 or may be metal rings, or other structures. Notches 14 may be spaced at either regular or irregular positions along the length of catheter wall 50, and preferably extend around the entire diameter of catheter wall 50. Alternatively, notches 14 may be positioned on the side of catheter 10 to be compressed, with strengthening members positioned on the opposite side of catheter 10.

Notches 14, which are non-linear V-shaped slots or angled wedge indentations, include narrow apex 56 adjacent interior surface 52 and a wider top opening 58 adjacent outer surface 44 of catheter wall 50. Top opening 58 is approximately 0.305 mm (0.012 inches) in width, although the width of opening 58 may vary. Notch 14 is approximately 0.305 mm to 0.381 mm (0.012 to 0.015 inches) in length axially. Apex 56 does not completely extend to interior surface 52. There is an approximate 0.254 mm to 0.381 mm (0.010 to 0.015 inches) space or gap between apex 56 and interior surface 52, although this may vary. The material comprising catheter wall 50 may vary axially, and preferably comprises a higher durometer, stiffer material composition proximate apex 56 and a lesser durometer, softer material composition proximate top opening 58. Catheter wall material is removed to form notches 14 when notches 14 are molded in catheter wall 50. As a result, notches 14 provide a means for taking up the catheter material as notches 14 are compressed and catheter 10 is bent. The area between notches 14 is thicker since the area comprises more catheter wall material which may be used as a strengthening member for catheter 10. Strengthening members, discussed below, may be optionally employed and positioned between notches 14 to stiffen catheter wall 50.

Notches 14a, shown in FIG. 4, include apex 60, fulcrumed nonlinear walls 62, and wide top opening 64, and are positioned within catheter wall 50. Apex 60 is adjacent interior surface 52 of catheter wall 50, but there is approximately 0.010 inches between apex 60 and interior surface wall 52, although this may vary. Fulcrumed walls 62 are concave and semi-spherical, and are positioned between wires 24 and interior surface 52. Top opening 64, adjacent outer surface 54 of catheter wall 50, is approximately 0.305 mm (0.012 inches) in width, although this may vary. Notches 14a are approximately 0.305 mm to 0.381 mm(0.012 to 0.015 inches) in length axially.

The slot size, or amount of catheter wall material removed, of notches 14 may also vary among different notches, and is determined by the application for which catheter 10 is utilized. In addition, the width of top opening 58, 64, slot size of notches 14, 14a and the spacing of the notches determine the ease of bending catheter 10. If the width of the opening 58, 64 of slot or notch 14, 14a and the slot size of notch 14, 14a is very small, outer sheath 28 will bend very little. Close spacing of notches 14, 14a allows catheter 10 to bend in more locations and in a tighter radius. Notches 14, 14a allow catheter 10 to bend more with exertion of less force, relative to other catheters, while retaining the circular identity of catheter 10.

Figure 5:
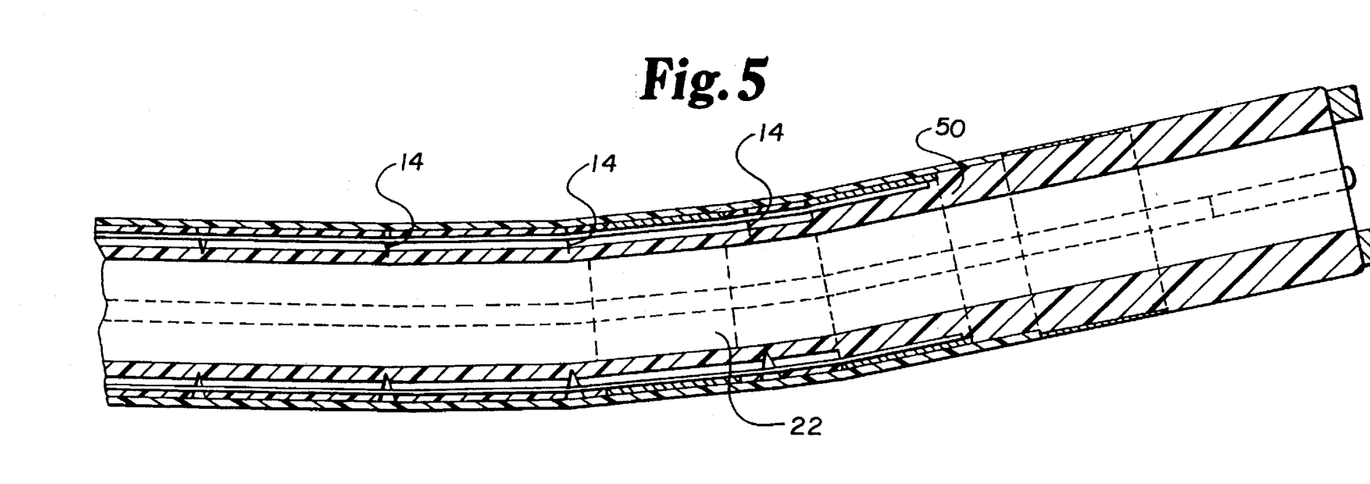
FIG. 5 is a side sectional view of a portion of the catheter in a bent configuration.
Figure 6:
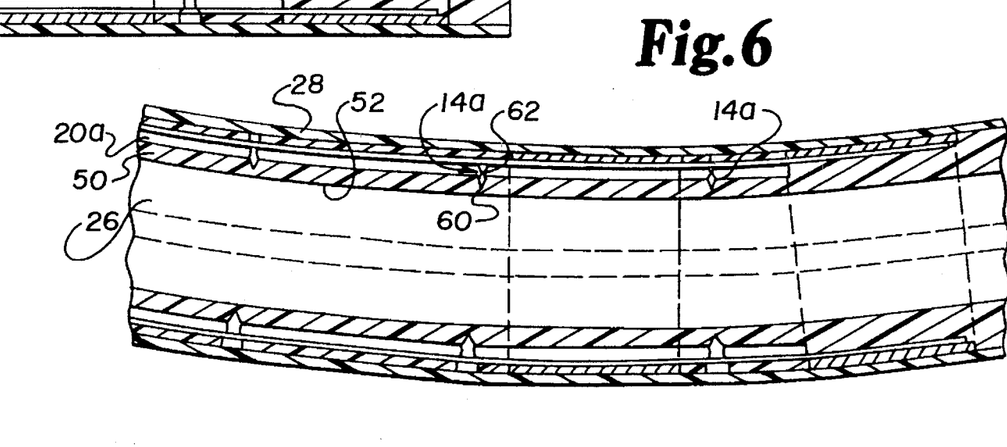
FIG. 6 is a side sectional view of a portion of the catheter in a bent configuration of the alternate embodiment depicted in FIG. 4.

In addition, the slot opening width and spacing of notches 14, 14a may be utilized to prevent over-bending or collapsing of inner lumens in catheter 10, such as wire access lumens 20. Preferably, the slot top opening width of notches 14 and the spacing of notches 14 are such that when catheter 10 is in a bent configuration, the notches 14 close in a direction in which catheter 10 is bent, as shown in FIG. 5. In the alternative embodiment in FIG. 4, the fulcrum configuration of the walls of notch 14a results in the compression being dissipated outwardly at apex 60, as indicated by the arrows 66. The top edges 68 of notch 14a come together to close the notch opening 64 of notch 14a as catheter 10 is bent. Notch opening 64 is subjected to tension forces when catheter 10 is in a bent configuration as indicated by the arrows 70 in FIG. 4. The tension created in bending catheter 10 causes top edges 68 and fulcrumed walls 62 of notch 14a to be compressed toward one another in the direction in which catheter 10 is bent, as shown in FIG. 6.

Figure 2D:
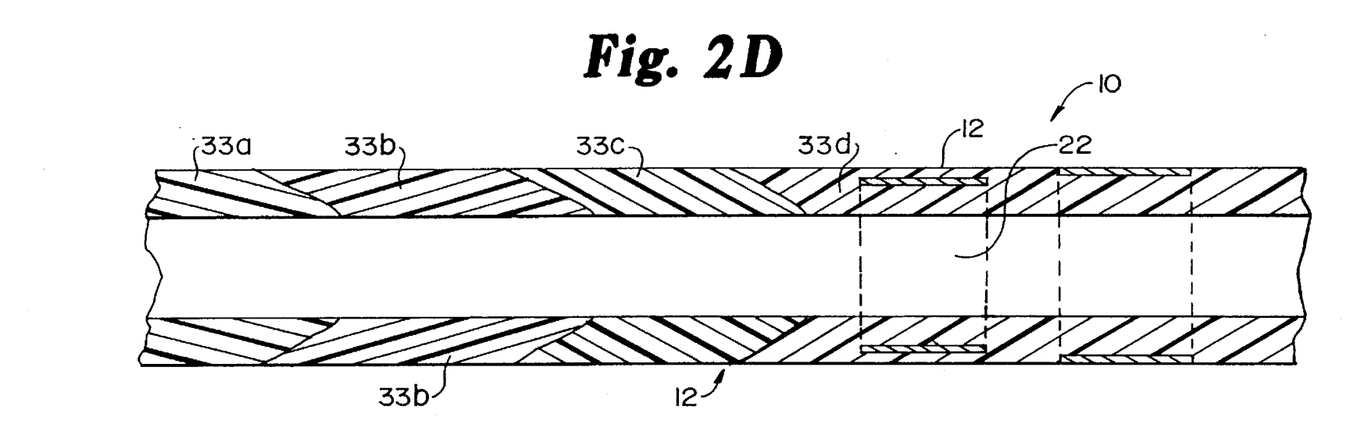
FIG. 2D is a side sectional view of a portion of an alternate embodiment of the catheter comprising different durometer materials.
Figure 2E:
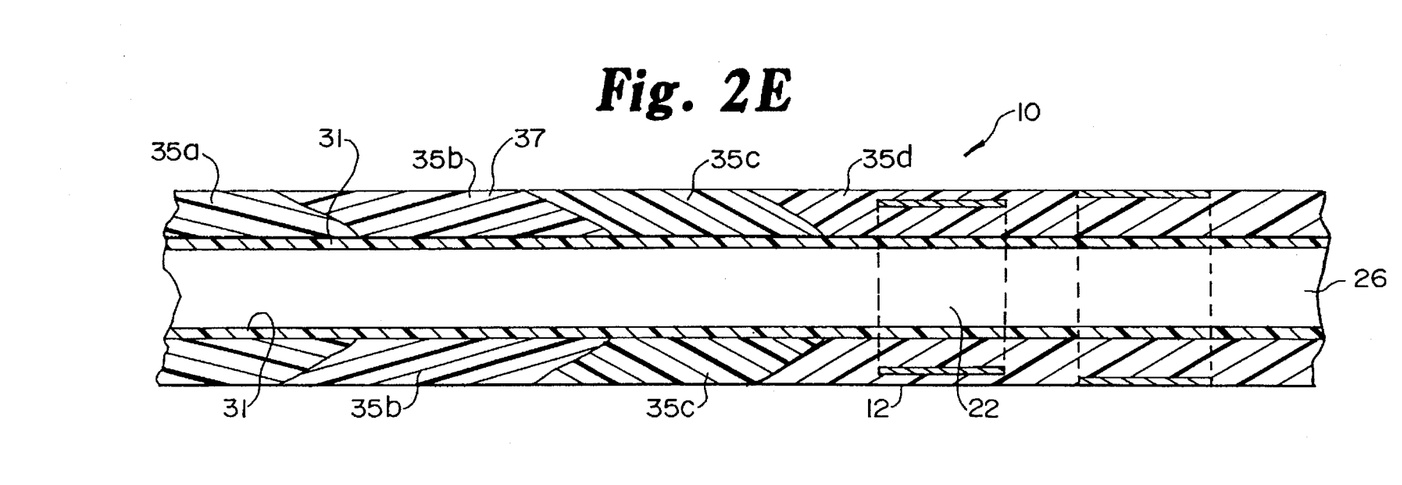
FIG. 2E is a side sectional view of a portion of an alternate embodiment of the catheter different durometer materials.

Steering enhancement regions may also be utilized in the invention. The steering enhancement regions may comprise consecutively softer, lower durometer materials along the length of the catheter body 12 as catheter 10 progresses from proximal end 30 adjacent handle 16 towards distal end 32. In addition, steering enhancement regions in the tubular body of the catheter wall 50 at distal end 32 of catheter body 12 may comprise lower durometer materials than areas adjacent to the steering enhancement regions. Alternatively, the tubular body of the catheter wall 50 in catheter body 12 may comprise a higher durometer material 29 proximate central lumen 26 of catheter 10, with a lower durometer material 31 proximate outer sheath 28 of catheter 10, as shown in FIG. 2D. As shown in FIG. 2D, material 31 may comprise longitudinally extending wedge regions comprising different durometer materials, as shown by regions 33a, 33b, 33c, 33d, with regions 33a, 33b, 33c, 33d being of a lower durometer than material 29. Alternatively, material 31 may be of only one durometer, having a lower durometer than material 29. The higher and lower durometer materials used for steering enhancement in catheter body 12 at distal end 32 may overlap. For example, as shown in FIG. 2E, catheter body 12 may have tapered, longitudinally extending wedge steering enhancement regions comprising different durometer materials, as shown by regions 35a, 35b, 35c, 35d. Preferably, 35a is of a higher durometer than 35b, and 35a is of a higher durometer material than 35d. As shown in FIG. 2E, the wedge or tapered shape of regions 35a–d overlap axially and comprise a material composition having mechanical characteristics differing from the characteristics of the adjacent regions. Catheter 10 may include numerous regions 35 of varying durometers throughout the length of the catheter to aid in the articulation of the catheter. Preferably, regions 35 of varying durometers do not extend beyond anchoring rings 22.

The steering enhancement region may also be a steering enhancement indentation region in the tubular body of the catheter wall 50 proximate distal end 32 of catheter body 12. The steering enhancement indentation region may comprise a plurality of circumferential indentations within the catheter wall 50 arranged so that the catheter wall 50 in each region comprises varying durometers. Each of the plurality of indentations comprises a material composition having mechanical characteristics differing from the characteristics of the adjacent indentation. The plurality of indentations extend between and do not intersect the outer surface 54 and the interior surface 52 of catheter 10. The indentation region may comprise locations having a material composition that is more pliable and of a lower durometer than portions of the tubular body proximate the interior surface 52 of the catheter wall 50 and locations having a material composition that are less pliable and of a higher durometer than other portions of the tubular body proximate the outer surface 54 of the catheter wall 50.

Figures 7, 8, 9, 10, 11, 12, 13, 14, 15, 16, 17, 18:
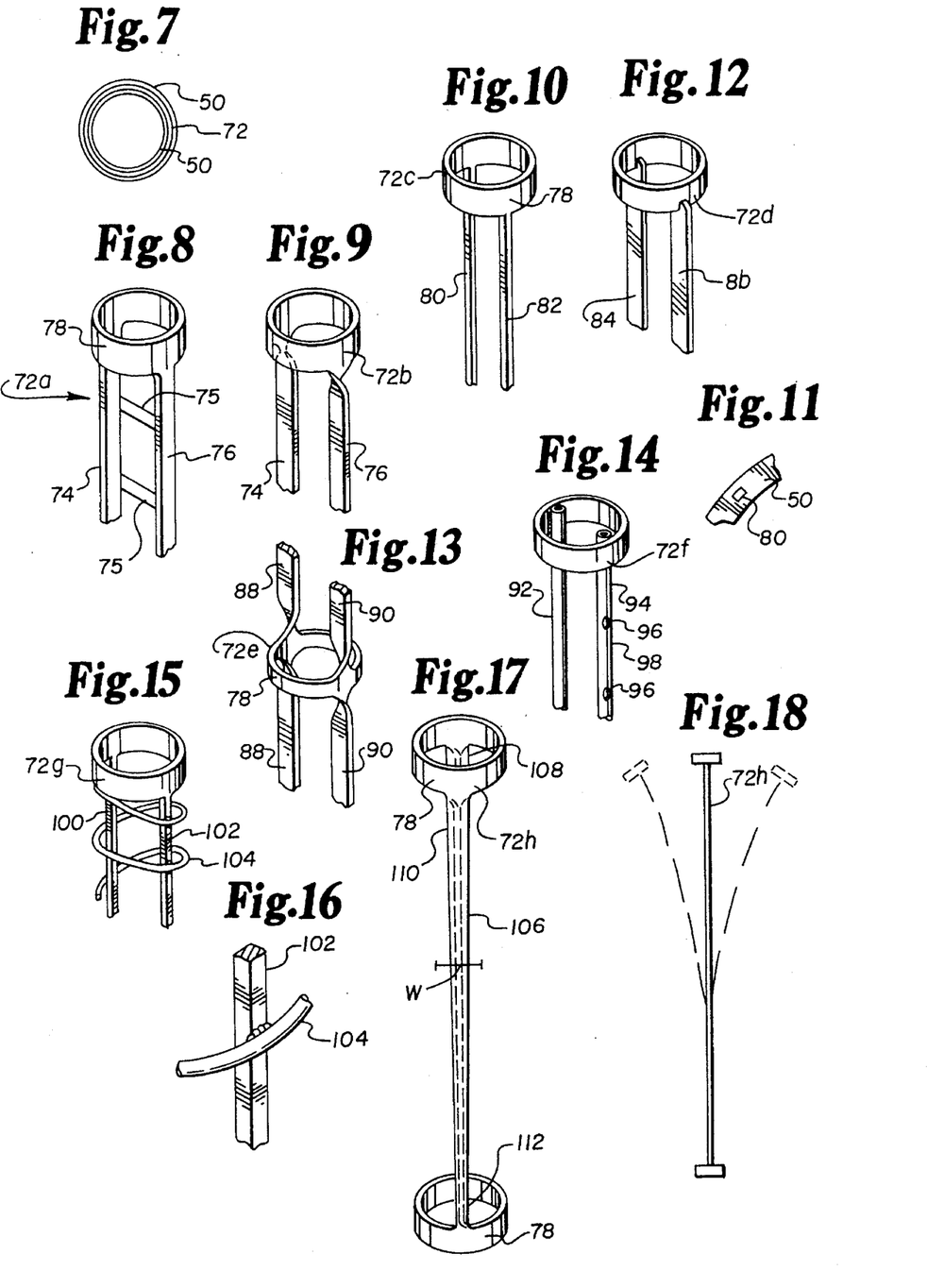
FIG. 7 is a simplified transverse sectional diagram without sectional hatching of a strengthening member positioned within a catheter.
FIG. 8 is a fragmentary perspective of one embodiment of an integral strengthening member.
FIG. 9 is a fragmentary perspective of an alternative embodiment of an integral strengthening member which has been rotated 90 degrees.
FIG. 10 is a fragmentary perspective of an alternative embodiment of an integral strengthening member having square struts.
FIG. 11 is a cross section view of a portion of the diagram in FIG. 7 showing the positioning of one of the struts in the strengthening member in FIG. 10.
FIG. 12 is a fragmentary perspective of an alternative embodiment of a strengthening member having attached struts.
FIG. 13 is a fragmentary perspective of an alternative embodiment of a strengthening member having intermittent ring structures.
FIG. 14 is a fragmentary perspective of an alternative embodiment of a strengthening member having tubular struts with apertures.
FIG. 15 is a fragmentary perspective of an alternative embodiment of a strengthening member having a helical coil.
FIG. 16 is an enlarged fragmentary view of the attachment of the helical coil shown in FIG. 15.
FIG. 17 is a fragmentary perspective view of an alternative embodiment of a strengthening member which is tapered along its length.
FIG. 18 is a side elevational mechanical diagram of the strengthening member shown in FIG. 17 showing the flexure taking place in one plane.

Referring to FIG. 7, a simplified transverse sectional diagram, without sectional hatching, of a strengthening member 72 positioned within catheter wall 50 is shown. Strengthening members 72 may axially extend substantially the entire length of catheter 10, or may optionally be positioned axially in only a selected portion of catheter wall 50, such as near tip 18. In addition, strengthening members 72 may extend in a radial orientation in catheter wall 50. Strengthening members 72 provide support for and retain the circular integrity of steerable catheter 10, especially when catheter 10 is in a bent state or when catheter 10 includes multiple wire access lumens. A number of configurations may be used for strengthening members 72, such as springs, metallic rings, tubular structures, struts, braiding, thickened areas of catheter wall material, or different choices of materials so that some portions of catheter wall 50 include a more pliable, softer material or a less pliable, harder material, such as a plastic. Strengthening members 72 preferably comprises a material having some flexibility so that strengthening members 72 can bend as catheter 10 is articulated, yet will not stretch or compress. Strengthening members 72 are particularly advantageous for providing compressive strength during use of catheter 10. A number of materials may be used for strengthening members 72, such as stainless steel, polycarbonate, or a high durometer plastic material, such as nylon. Strengthening members are generally about to 0.002–0.020 inches (0.05 to 0.051 mm) in thickness, preferably 0.002 inches thick.

FIG. 8 is a fragmentary perspective view of one embodiment of strengthening member 72. As shown in the embodiment in FIG. 8, strengthening member 72a is formed from a generally tubular structure from which a substantial amount of material has been removed, such as by an electrical discharge machine. The amount of material removed to form strengthening member 72a may vary, depending on the amount of flexibility desired in the end use configuration. Strengthening member 72a is preferably an integral piece after the material is removed. As shown in the embodiment in FIG. 8, struts 74, 76 are essentially rectangular in shape, and are integral with ring 78. Preferably two struts 74, 76 are utilized, although this may vary. Strengthening member 72a preferably extends axially through catheter 10. As the embodiment in FIG. 8 illustrates, and is applicable to any of the strengthening member embodiments in FIGS. 8–10 and FIGS. 11–15, strengthening member 72a may include radial ribs or supports 75 extending between struts 74, 76 for providing additional strength and support in strengthening member 72a.

Referring to FIG. 9, a fragmentary perspective view of an alternate integral embodiment of strengthening member 72 is shown. The embodiment in FIG. 9 is similar to the FIG. 8 embodiment, except that struts 74, 76 are twisted and maneuvered approximately ninety (90) degrees during manufacturing to align struts 74, 76 on a longitudinal axis with respect to catheter 10. The maneuvering angle may vary. Twisting of struts 74, 76 permits bending of strengthening member 72b during bending of catheter 10. Preferably two struts 74, 76 are utilized, although this may vary. Strengthening member 72b is utilized, for example, in applications requiring strong tension or compression for flexure in one axis. Strengthening member 72b preferably extends axially through the length of catheter 10.

FIG. 10 is a fragmentary perspective view of an alternate integral embodiment of strengthening member 72. Struts 80, 82 of strengthening member 72c are integrally attached to ring structure 78. Struts 80, 82 in this embodiment are substantially square in cross section. Preferably two struts 80, 82 are utilized, although this may vary. Strengthening member 72c may be used in applications requiring, for example, the same flexure as strengthening member 72b in FIG. 9 but which requires less tension-compression. Strengthening member 72c preferably extends axially through the length of catheter 10.

FIG. 11 is a fragmentary cross section view of strengthening member 72c in FIG. 10 positioned within catheter wall 150. Strut 80 is substantially square in cross section. The position of strut 80 within catheter wall 150 in FIG. 11 also applies to any of the other strengthening member embodiments in, for example, FIGS. 8–10, 12–15, and 17.

Referring to FIG. 12, a fragmentary perspective view of an alternate embodiment of strengthening member 72 is shown. Strengthening member assembly 72d includes a ring structure 78 to which separate struts 84, 86 are attached by soldering, welding, bonding, or other suitable means. Preferably two struts 84, 86 are utilized, although this may vary. Strengthening member 72d preferably extends axially through catheter 10. Strengthening member 72d may be used in applications requiring, for example, ease of manufacturing since integral units are more difficult to produce.

As shown in the embodiment in FIG. 13, a fragmentary perspective view of an integral alternate embodiment of strengthening member 72 having intermittent rings is illustrated. Struts 88, 90 of strengthening member 72e are integrally attached to ring structure 78. Struts 88, 90 are twisted and maneuvered approximately ninety (90) degrees during manufacturing to align struts 88, 90 on a longitudinal axis with respect to catheter 10. The maneuvering angle may vary. Twisting of struts 88, 90 permits bending of strengthening member 72e during bending of catheter 10. Preferably two struts 88, 90 are utilized, although this may vary. Intermittent ring structures 78 may be positioned axially within catheter 10. The intermittent positioning of ring structures 78 along the length of catheter 10 allows for segmentation for flexure of catheter 10. Ring structure 78 may be positioned at random, irregular, or at regular intervals along the length of catheter 10. The use of the intermittent ring structures may be used equally well with the other embodiments of strengthening members 72, such as FIGS. 10 and 12. Strengthening member 72e may be used in applications requiring, for example, improved radial strength. Strengthening member 72e preferably extends axially through the length of catheter 10.

Referring to FIG. 14, a fragmentary perspective view of an alternate embodiment of strengthening member 72 is shown. Strengthening member 72f comprises a plurality of hollow tubular elements 92, 94 attached by soldering, welding or other means to a ring structure 78. Preferably two struts or tubular elements 92, 94 are utilized, although this may vary. As the embodiment in FIG. 14 illustrates, tubular elements 92, 94 may comprise a hollow tubular structure, or may alternatively comprise a hollow tubular structure having a plurality of holes or apertures 96 formed through a portion of wall 98 of the tubular element. Strengthening member 72f may comprise a plurality of struts, and may comprise struts having both apertures and struts having no apertures. Preferably, two tubular elements 92, 94 are utilized, although this may vary. Aperture 96 does not extend all the way through tubular element 94. Tubular element 94 may be particularly advantageous in applications where wires or other means pass through tubular element 94, since apertures 96 provide an exit passage along the perimeter of tubular element 94 for connection of the wires or other means to, for example, the electrodes. Apertures 96 may be positioned at random, irregular, or at regular intervals along the length of tubular element 94. Strengthening member 72f preferably extends axially through the length of catheter 10.

FIG. 15 is a fragmentary perspective view of an alternate embodiment of strengthening member 72. Struts 100, 102 of strengthening member 72g are integrally attached to ring structure 78, and struts 100, 102 may comprise different shapes, as discussed above. A helical spring coil 104 may be wound and positioned around struts 100, 102 to provide additional rigidity to strengthening member 72g, while still allowing for flexibility. Preferably two struts 100, 102 are utilized, although this may vary. Strengthening member 72g preferably extends axially through the length of catheter 10. FIG. 16 is an enlarged fragmentary view of FIG. 15 showing the attachment of coil 104 to strut 102 by welding, soldering, or other appropriate means.

FIG. 17 is a fragmentary perspective view of an alternate embodiment of strengthening member 72. Strengthening member 72h comprises struts 106, 108 extending between ring structures 78. Struts 106, 108 are generally rectangular walls which are tapered by removal of material to result in a generally straight taper extending between ring structures 78. Strengthening member 72h has less flex at end 110 where struts 106, 108 are thicker, and has more flexing capability at end 112, where struts 106, 108 are less thick because more material is removed. The taper of struts 106, 108 may be varied to achieve the desired flexing profile for catheter 10. Struts 106, 108 can also vary radially by varying the width W or thickness of struts 106, 108 at various points along the length of struts 106, 108 to achieve the desired flexing profile. Struts 106, 108 are twisted and maneuvered approximately ninety (90) degrees during manufacturing to align struts 106, 108 on a longitudinal axis with respect to catheter 10, although this angle may vary. Twisting of struts 106, 108 permits bending of strengthening member 72h during bending of catheter 10. Preferably two struts 106, 108 are utilized, although this may vary. Strengthening member 72h changes the density of the internal structure of catheter 10. Strengthening member 72h preferably extends axially through the length of catheter 10.

FIG. 18 is a side elevational mechanical diagram view of strengthening member 72h embodiment in FIG. 17. Strengthening member 72h permits flexing in alignment with struts 106, 108 which are diametrically opposed. Flexure of strengthening member 72h occurs in one plane on a single axis, as shown in the embodiment in phantom lines in FIG. 18.

Figures 19, 20:
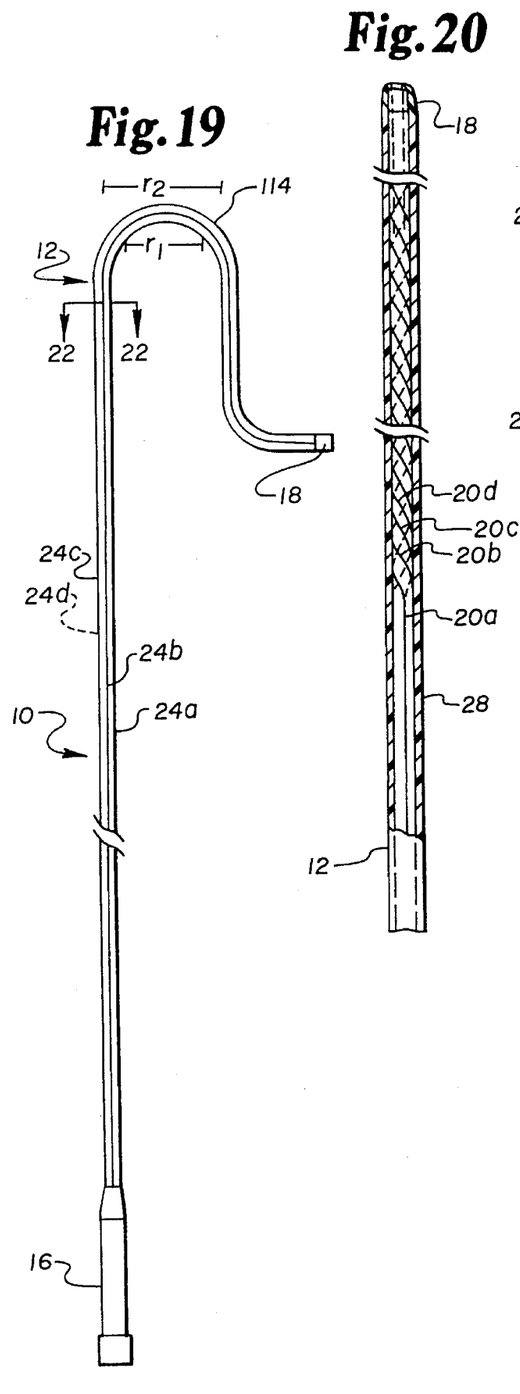
FIG. 19 is a side elevational view of a catheter having wire access lumens in a straight configuration.
FIG. 20 is a fragmentary enlarged side view of a catheter, with a part cut away, having helical wire access lumens.

In the catheter embodiments of FIGS. 2–6, wire access lumens 20 are a generally straight passageway through catheter body 12 from proximal end 30 toward distal end 32 of catheter 10. Pull wires 24 are inserted into wire access lumens 20 and are used to pull on catheter tip 18 to articulate and steer tip 18. If catheter shaft or catheter body 12 is configured in a straight line and tip 18 is articulated into a certain configuration, rotation of catheter shaft about its long axis will not deflect or change the shape of tip 18 because the length of wires 24 remains constant during catheter rotation. However, if catheter body 12 is curved in an area different from distal tip 18, as shown in FIG. 19, then one pull wire 24 must be longer than the other pull wire 24 in the area where catheter body 12 is curved. As catheter 10 is rotated 180 degrees, the pull wire 24 which is the shortest since it is on the smallest radius $r_1$ of the bend 114 must become the longest, and the longest wire since it is in the largest radius $r_2$ of the bend must become shortest, as shown in FIG. 19. The resulting effect is to change the shape of tip 18 since this action is identical to changing the shape of tip 18 by using pull wires 24. It is not always desirable to have coupling between rotation of the catheter 10 and the shape of tip 18. Preferably, the catheter can be rotated without changing the shape of catheter 10.

FIG. 19 illustrates a side elevational view of catheter 10, with outer sheath 28 and catheter body 12 removed to expose wires 24a, 24b, 24c, and 24d. Catheter 10 is curved or bent in a tight radius bend in response to body arches or curves, resulting in a curved area 114 in catheter 10 proximal to distal tip 18, and a reverse curve response in tip 18 because of the position of wire access lumens 20. As a result, wires 24c, 24d in wire access lumens 20 are longer than wires 24a, 24b in area 114. As catheter 10 is rotated using handle 16, wires 24a, 24b are positioned where wires 24c, 24d were positioned, and wires 24c, 24d become positioned where wires 24a, 24b were positioned.

Figures 21, 22:
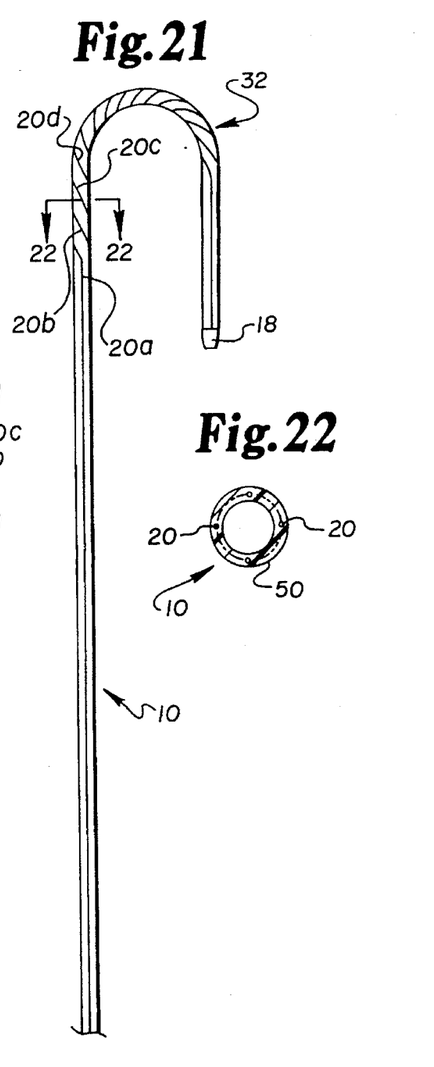
FIG. 21 is a fragmentary side elevational view of a catheter having helical wire access lumens.
FIG. 22 is a section view taken along line 22—22 in FIG. 19 and FIG. 21.

Referring to FIG. 20 and FIG. 21, an alternative embodiment of catheter 10 is shown. FIG. 20 is a fragmentary enlarged side view of catheter 10 with a portion of catheter 10 cut away. As shown in FIG. 20, wire access lumens 20a, 20b, 20c, 20d including pull wires 24 are arranged in a helical orientation in catheter 10. Preferably, the helically wound wire access lumens 20 are positioned in the most distal eighteen (18) to twenty four (24) inches (approximately 45.7 cm to 61 cm) of catheter body 12 in catheter 10 proximate tip 18, approximately twenty to thirty diameters based on catheter 10 before tip 18, without extending into tip 18. Wire access lumens 20 are substantially straight proximal tip 18 and in the proximal end 30 of catheter 10. However, it is possible to selectively choose where in catheter 10 to position the helical passageways of wire access lumens 20. The helical passageways formed by wire access lumens 20 need not extend through the entire eighteen to twenty four inches at distal end 32 of catheter 10. Preferably, for an approximate 100 cm (approximately 39.4 inches) long catheter 10 curved in a 5 cm (2 inch) radius, there will be three to four, preferably four, helical bends of wire access lumens 20 to minimize the effect of catheter rotation. The helical configuration of wire access lumens 20 is preferred in catheters having off center wires 24.

FIG. 21 is a fragmentary side elevational view illustrating the distal end 32 of catheter 10 with outer sheath 28 removed. Wire access lumens 20a, 20b, 20c, 20d are positioned in a helical arrangement at the distal end of catheter 10 where catheter 10 is curved, and are substantially straight proximal tip 18. The helical configuration of wire access lumens 20 provide compression for bending of distal end 32 of catheter 10, without the reverse curve response of tip 18 seen in FIG. 19. The helical arrangement of wire access lumens 20 ensures that the length of pull wires 24 is independent of the catheter shaft shape, so that an articulated arch shape 114 is achieved.

FIG. 22 is a section view taken along line 22—22 of FIG. 19 and FIG. 21. As shown in FIG. 22, the cross section view is essentially identical in both catheters. The same action is used to pull on wires 24.

The catheter of the present invention may function as a steerable guiding and mapping catheter. A surgical catheter, such as a laser catheter, may be inserted through central lumen 26 to a target site to perform a surgical procedure. In another configuration, catheter 10 may itself be used to locate particular tissue during a surgical procedure and then destroy the tissue as needed if an ablation electrode is used, without the insertion of another catheter. Steerable catheter 10 is especially useful in electrophysiology applications, although catheter 10 may be used in a wide variety of medical procedures.

In operation, catheter 10 is inserted into the patient. The cardiologist or other user of catheter 10 controls the direction of catheter 10 distal tip 18 using platform handle 16 to apply tension on selected wires 24a, 24b which are attached to steering rings 22. If a wire positioned in wire access lumen 20a is pulled, catheter tip 18 will bend in a particular direction adjacent the steering ring 22 to which the selected wire is attached. If a wire positioned in wire access lumen 20b is pulled, catheter 10 will bend in another direction. Steering enhancement means, such as the above notches 14, 14a, greatly aid in the movement, bending, and control of catheter 10. Undesired compression of wire access lumens 20 is reduced or eliminated by these novel notch configurations. The ability to pull wires 24 at different sites of steering rings 22 along the length of catheter 10, coupled with the additional pliability provided by the notches, results in improved, smooth maneuverability, control, and steerability of the catheter within the patient's body. The ability to lock catheter tip 18 in position is also advantageous to the smooth control of catheter 10 since it reduces the user intervention of applying force to the knob, holding the handle in place or locking a cam during the medical procedure.

Catheter 10 with notches 14, 14a provides improved repeatability and has an active return capability so that the device does not rely solely on the resilience of the catheter material to return to its previous position. Since catheter 10 is pulled at various points along its length, rather than only at its distal end or tip, there is less stress on the catheter material because there is less compression. As a result, the operator can maneuver the catheter by pulling back on the wires knowing that the catheter will respond in the same way each time the catheter is pulled a certain distance. Thus, the catheter has a longer life expectancy and the elasticity of the catheter 10 is preserved for a longer period of time.

The speed and fineness of control of catheter 10 is also a distinct advantage of this invention. Bends are made quicker because of the ability to bend catheter 10 throughout much of the entire length of catheter 10. As a result, the operator has more control of catheter 10. Also, catheter 10 may be positioned much more quickly than other steerable catheters since it is not necessary to bring the catheter tip into and out of an outer sheath for shaping purposes. This may also reduce the occurrence of trauma to endothelial linings within arteries or other structures. In addition, when catheter 10 is used as a guiding catheter, a significant time savings results since a different type of catheter may be inserted without requiring removal of the guiding catheter and re-location of the affected tissue with a second catheter. In addition, the straight, continuous central lumen provides an easy passage of the other catheter through catheter 10 without the other catheter getting caught in or hooked on an irregularly shaped central lumen surface.

The use of strengthening members in the area of catheter 10 which articulates is also advantageous. Strengthening members prevent the collapse of the catheter or distortion of the catheter into a non-circular shape during large articulations or after several small articulations of the catheter. Preventing the collapsing of the catheter using the strengthening members aids in the passage of a catheter through the central inner lumen of catheter 10.

It is also advantageous to use helical passageways comprising wire access lumens 20 for pull wires 24 since the length of pull wires 24 is independent of the catheter shaft shape. By having helical passageways, pull wires 24 spend equal amounts of time on the long side or radius and the short side or radius of the catheter bend. Depending on the number of helical turns, the effect of catheter rotation on the distal shape can be minimized. The more helical bends in the distal end of the catheter, the less effect catheter rotation will have on the length of the pull wires 24. In addition, the amount of force necessary to rotate the catheter in a bent configuration does not change during catheter rotation when the helical configuration of the wire access lumens is used at the distal end of the catheter. As the change in length of the pull wires becomes smaller, the uniformity of the torque becomes greater throughout the catheter. In a catheter have the wire access lumens in a straight configuration is used, changes in force occur because a force is necessary to change the length of the pull wires.

The catheter may also have a balancing and sensing sub-system for monitoring wire elongation. The sub-system determines the stress on the wires and may compensate for any deformation of wire or catheter body material which may develop after repeated use of the catheter.

We claim:

1. A steerable wire guiding catheter, comprising:
   a) an elongate catheter body having a catheter wall, a distal end, a proximal end, the catheter wall being comprised of a generally tubular body presenting an interior surface and an outer surface;
   b) a plurality of wire means, each wire means having a proximal end and a distal end and extending through the tubular body of the catheter wall for pulling on a steerable portion of the catheter wall integral with and proximate to the distal end of the catheter body to effect steering of the catheter;
   c) a plurality of anchor means, each anchor means corresponding to a distal end of one of the wire means and axially located along the steerable portion of the catheter wall of the catheter body for connection with a distal end of the respective one of the wire means; and
   d) control means located at a proximal portion of the catheter for controlling the pulling on the proximal end of the wire means.

2. The catheter of claim 1 wherein the plurality of wire means pulls on a steerable portion of the catheter wall integral with and proximate to the distal end of the catheter body.

3. The catheter of claim 1 further comprising radial placement of a material composition stiffer than the tubular body proximate the interior surface and a material composition softer than the tubular body proximate the outer surface of the catheter wall.

4. A steerable wire guiding catheter, comprising:
  a) an elongate catheter body having a catheter wall, a distal end, a proximal end, the catheter wall being comprised of a generally tubular body presenting an interior surface and an outer surface;
  b) a plurality of wire means, each wire means having a proximal end and a distal end and extending through the tubular body of the catheter wall for pulling on a steerable portion of the catheter wall integral with and proximate to the distal end of the catheter body to effect steering of the catheter, the wire means following a generally helical path over a portion of the axial length of the catheter proximal the distal end of the catheter;
  c) a plurality of anchor means, each anchor means corresponding to a distal end of one of the wire means and axially located along the steerable portion of the catheter wall of the catheter body for connection with a distal end of the respective one of the wire means; and
  d) control means located at a proximal portion of the catheter for controlling the pulling on the proximal end of the wire means.

5. The steerable catheter of claim 4 further comprising a strengthening member axially positioned within the catheter.

* * * * *